(12) United States Patent
Alromaih et al.

(10) Patent No.: US 10,772,650 B1
(45) Date of Patent: Sep. 15, 2020

(54) UNCINECTOMY KNIFE

(71) Applicant: KING SAUD UNIVERSITY, Riyadh (SA)

(72) Inventors: Saud Romaih Alromaih, Riyadh (SA); Ibrahim Ali Sumaily, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 16/734,162

(22) Filed: Jan. 3, 2020

(51) Int. Cl.
*A61B 17/24* (2006.01)
*A61B 17/32* (2006.01)

(52) U.S. Cl.
CPC ...... *A61B 17/24* (2013.01); *A61B 17/320016* (2013.01); *A61B 2017/320074* (2017.08)

(58) Field of Classification Search
CPC . A61B 17/24; A61B 17/32; A61B 17/320016; A61B 2017/32006; A61B 17/3205; A61B 17/3209; A61B 17/3211
See application file for complete search history.

(56) References Cited

U.S. PATENT DOCUMENTS

| | | | |
|---|---|---|---|
| 5,397,333 A | 3/1995 | Knoepfler | |
| 5,470,339 A | 11/1995 | Lerrick | |
| 8,377,064 B2 | 2/2013 | Wallis | |
| 8,608,763 B1* | 12/2013 | Jurbala | A61B 17/320036 606/170 |
| 2004/0127927 A1 | 7/2004 | Adams | |
| 2010/0100111 A1 | 4/2010 | Rogerson | |
| 2011/0021975 A1* | 1/2011 | Covello | A61B 17/24 604/22 |
| 2013/0144318 A1 | 6/2013 | Dinis Carmo | |
| 2015/0045821 A1* | 2/2015 | Darian | A61B 17/14 606/170 |
| 2019/0240005 A1 | 8/2019 | Rosenthal et al. | |

* cited by examiner

*Primary Examiner* — Matthew J Lawson
*Assistant Examiner* — Lisa Nguyen
(74) *Attorney, Agent, or Firm* — Nath, Goldberg & Meyer; Richard C. Litman

(57) ABSTRACT

The uncinectomy knife is a surgical knife for performing uncinectomies and other sinus or endoscopic procedures. The uncinectomy knife has a central elongated handle having opposing first and second ends. The knife has a horizontally oriented cutting blade extending orthogonally from the first end of the handle and a vertically oriented cutting blade extending orthogonally from the second end of the handle. Both of the blades may be double-edged so that they can cut when the handle is moved in opposite directions. Both ends of each blade may terminate in a bulbous tip having a smooth, blunted surface, such as a sphere or rounded ball to prevent tissue trauma when the blade ends contact tissue. Accordingly, the uncinectomy knife may be inserted into tight cavities for tissue augmentation or removal without damaging the surrounding tissue.

4 Claims, 2 Drawing Sheets

UNCINECTOMY KNIFE

BACKGROUND

1. Field

The disclosure of the present patent application generally relates to a surgical knife, and particularly to an uncinectomy knife for removing the uncinate process in surgical procedures for improving drainage from the paranasal sinuses and removing obstacles to breathing.

2. Description of the Related Art

The uncinate process is a small part of the ethmoid bone housing the ethmoid infundibulum, and is located just lateral to the middle turbinate. The lower horizontal part of the uncinate process is attached to the upper edge of the inferior turbinate bone. The upper vertical part is attached to the lacrimal bone and terminates, attaching to the lamina papyrecia. In some people, the uncinate process may cause a blockage of the osteomeatal complex. As a result, the osteomeatal complex may not properly drain, and breathing may be hindered. Furthermore, sinus infections may be experienced more frequently due to improper drainage.

Endoscopic sinus surgery is one of the most common surgeries done on a daily basis, either for various sinus pathologies, or, since the last decade of the twentieth century, as an approach to the skull base. In these surgeries, uncinectomy (removal of the uncinate process from the ethmoid bone) is almost always the first step. This step is performed by one of several different techniques, often using multiple instruments. One of the most widely performed techniques involves using a backbiter to separate the vertical part of the uncinate process from the horizontal part of the uncinate process of the ethmoid bone. Then, either forceps or a tricot is used to remove the vertical part, and a through cut instrument is used to remove the horizontal part. Other techniques are considered less safe because they may carry risk of injury to the orbit and lacrimal system, or may end with incomplete uncinectomy or missing the natural ostium of the maxillary sinus.

Accordingly, several instruments are needed to perform an uncinectomy, and sometimes, even with this, it can be difficult to achieve a proper uncinectomy. Furthermore, these techniques are associated with a noticeable delay in the learning curve of endoscopic sinus surgery because it is difficult for beginners to master the above-mentioned technique.

Thus, an uncinectomy knife solving the aforementioned problems is desired.

SUMMARY

The uncinectomy knife is designed for performing uncinectomies and other sinus or endoscopic procedures. The uncinectomy knife has a central elongated handle having opposing first and second ends. The knife has a horizontally oriented cutting blade extending orthogonally from the first end of the handle and a vertically oriented cutting blade extending orthogonally from the second end of the handle. Both of the blades may be double-edged so that they can cut when the handle is moved in opposite directions. Both ends of each blade may terminate in a bulbous tip having a smooth, blunted surface, such as a sphere or rounded ball, to prevent tissue trauma when the blade ends contact tissue. Accordingly, the uncinectomy knife may be inserted into tight cavities for tissue augmentation or removal without damaging the surrounding tissue.

A method of removing an uncinate process from the ethmoid bone using the uncinectomy knife may include inserting the vertically oriented blade of the uncinectomy knife into a patient's nasal passage. The vertically oriented blade is then used to sharply and smoothly separate the upper and lower parts of the uncinate process to the lacrimal bone, achieving complete separation. Then, the instrument is reversed, and the horizontally oriented blade is used to separate the attachment of the uncinate superiorly from the lacrimal bone and the lower part from the inferior turbinate bone. In this manner, a single instrument may be used to perform uncinectomy in a few seconds, with less bleeding, traumatization, and instrumentation.

These and other features of the present disclosure will become readily apparent upon further review of the following specification and drawings.

DETAILED DESCRIPTION OF THE PREFERRED EMBODIMENTS

The present subject matter is directed to an uncinectomy knife designed for performing an uncinectomy and other sinus or endoscopic procedures. The uncinectomy knife has a central elongated handle having opposing first and second ends. The knife has a horizontally oriented cutting blade extending orthogonally from the first end of the handle and a vertically oriented cutting blade extending orthogonally from the second end of the handle. Both of the blades may be double-edged so that they can cut when the handle is moved in opposite directions. Both ends of each blade may terminate in a bulbous tip having a smooth, blunted surface, such as a sphere or rounded ball, to prevent tissue trauma to sensitive tissues, such as the septal mucosa, lateral nasal wall, orbit, middle and inferior turbinates, and flaps during insertion and manipulation of the knife 10, when the blade ends contact tissue. Accordingly, the uncinectomy knife may be inserted into tight cavities for tissue augmentation or removal without damaging the surrounding tissue.

Figure 1:
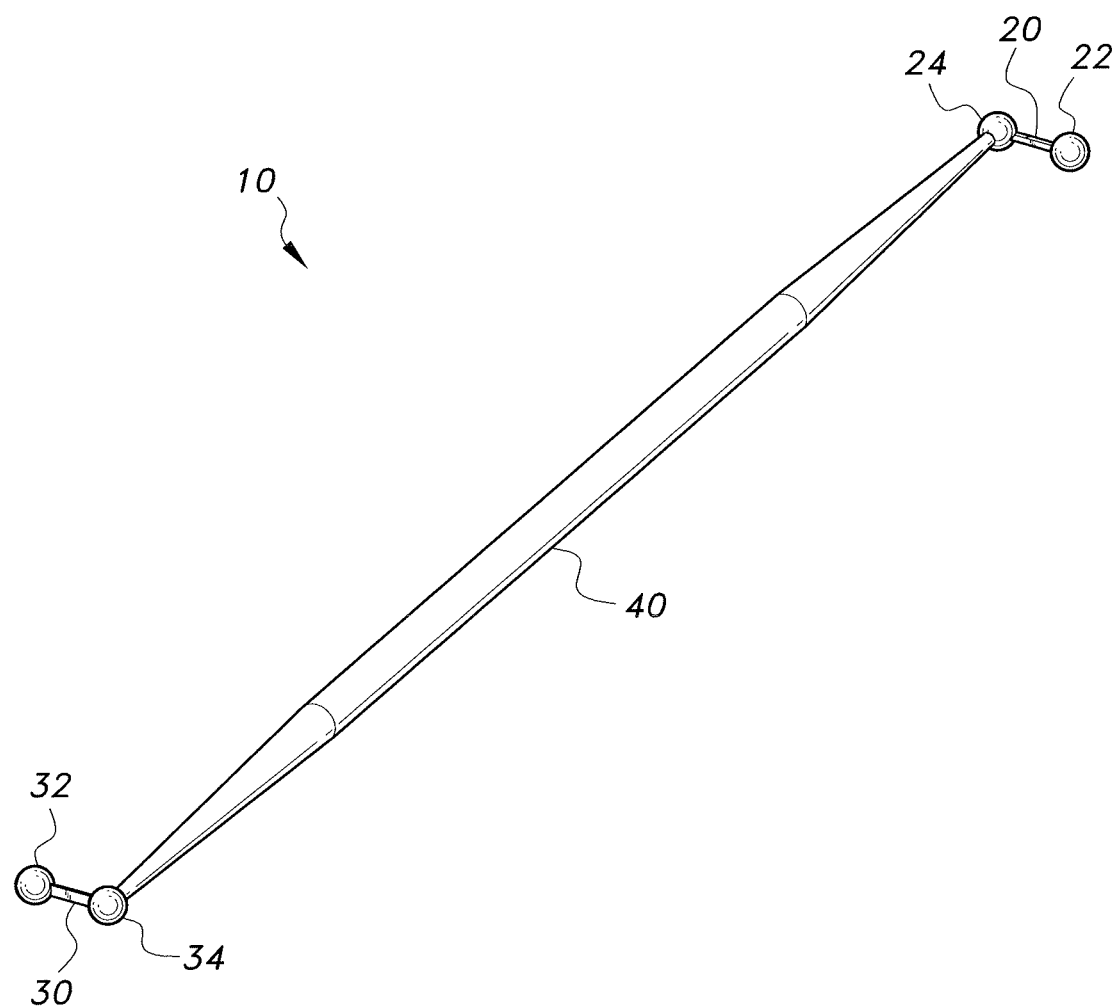
FIG. 1 is a perspective view of the uncinectomy knife.
Figure 2:
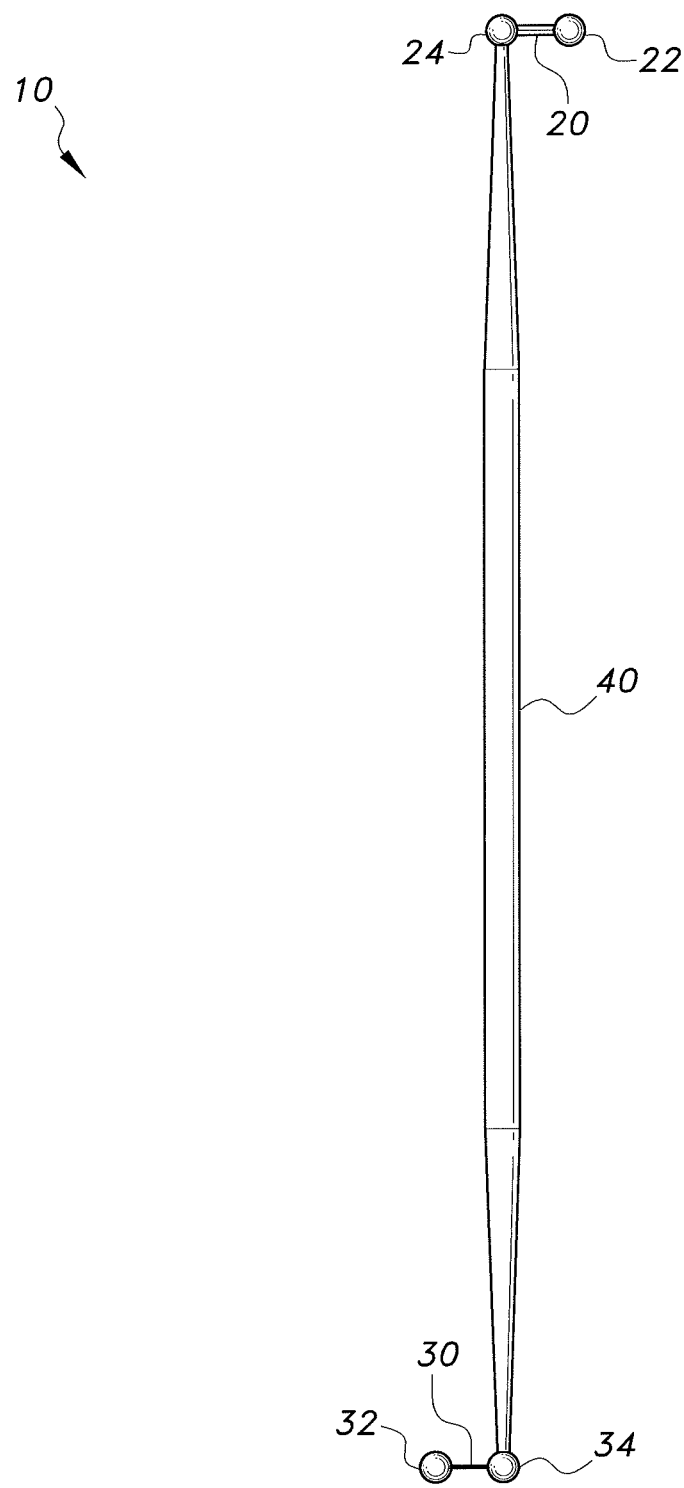
FIG. 2 is a front view of the uncinectomy knife of FIG. 1.
Similar reference characters denote corresponding features consistently throughout the attached drawings.

FIGS. 1 and 2 show an embodiment of the uncinectomy knife 10, for which the inventors have coined the term "uncinetome". The uncinectomy knife 10 includes a central elongated handle 40 to be manipulated by a hand of a practitioner. The handle 40 is generally cylindrical, the drawing sheet in FIG. 2 defining the plane of the handle. A first end of the handle 40 includes a horizontally oriented (i.e., the blade 30 may be a flat blade disposed in a plane perpendicular to a plane defined by the handle 40) blade 30 extending orthogonal to the handle 40. The horizontally oriented blade 30 is preferably double-edged. In FIG. 2, one edge of the blade 30 may extend forward from the drawing sheet, and the other edge may extend rearward from the drawing sheet. This enables the surgeon to use the horizontally oriented blade 30 by grasping the handle 40 and pulling the handle 40 forward or rearward. Both ends (i.e., the end of the blade 30 attached to the handle 40 and the free end of the blade 30) of the horizontally oriented blade 30 may terminate in a bulbous tip 32, 34 having a smooth, blunted surface, such as a sphere or rounded ball, to prevent tissue trauma when the blade ends contact tissue. The bulbous tip 32, 34 may define shapes other than a sphere, such as an ellipsoid, a semi-sphere, or a rounded-off blunt end. The shape of the bulbous tips 32, 34 may be selected based on the procedure, the constraints of the working area, and the preference of the practitioner.

A vertically oriented blade 20 extends orthogonally from the opposing second end of the handle 40. The vertically oriented blade 20 is also preferably double-edged and is oriented with the cutting edges aligned vertically in the plane of the handle 40. In FIG. 2, a first cutting edge faces upward in the plane of the drawing sheet and a second cutting edge faces downward in the plane of the drawing sheet. This enables the surgeon to use the vertically oriented blade 20 by grasping the handle 40 and pulling the handle 40 upward or downward. Both ends (i.e., the end of the blade 20 attached to the handle 40 and the free end of the blade 20) of the vertically oriented blade 20 may terminate in a bulbous tip 22, 24 having a smooth, blunted surface, such as a sphere or rounded ball, to prevent tissue trauma when the blade ends contact tissue. The bulbous tip 22, 24 may define shapes other than a sphere, such as an ellipsoid, a semi-sphere, or a rounded-off blunt end. The shape of the bulbous tips 22, 24 may be selected based on the procedure, the constraints of the working area, and the preference of the practitioner. Both blades 20, 30 extend orthogonally from the handle 40, and as seen most clearly in FIG. 2, may extend from the handle 40 in directions 180° opposite each other.

The handle 40 may have a length of about 15 cm, or in the range of 10 cm to 20 cm. The blades 20, 30 may have a length of about 3 mm, or in the range of 2 mm to 5 mm. The bulbous tips 22, 24, 32, 34 may have a diameter of about 1 mm, or in the range of 0.5 mm to 2 mm. The uncinectomy knife 10 may be made from stainless steel, carbon steel, or other material known in the art for making surgical scalpels.

A method of removing an uncinate process from the ethmoid bone using the uncinectomy knife 10 may include inserting the vertically oriented blade 20 into one of a patient's nasal passages. The vertically oriented blade is then used to sharply and smoothly separate the upper and lower parts of the uncinate process to the lacrimal bone, achieving complete separation. Then, the instrument is reversed, and the horizontally oriented blade is used to separate the attachment of the uncinate superiorly from the lacrimal bone and the lower part from the inferior turbinate bone.

The uncinectomy knife 10 may be used during a full range of endoscopic nasal surgeries, septoplasties, and other surgeries requiring inserting a cutting blade into confined areas. For example, the uncinectomy knife 10 may be used to cut bony edges, cartilage, and stitches.

It is to be understood that the uncinectomy knife is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. An uncinectomy knife, comprising:
    an elongated handle having a first end and an opposing second end, the handle defining a handle plane;
    a horizontally oriented blade extending orthogonally from the first end of the handle, the horizontally oriented blade having a first cutting edge and an oppositely facing second cutting edge, the first and second cutting edges of the horizontally oriented blade facing perpendicular to the handle plane, wherein the horizontally oriented blade has a first end attached to the handle and an opposing free second end, the horizontally oriented blade including a bulbous tip at the first and second ends of the blade; and
    a vertically oriented blade extending orthogonally from the second end of the handle, the vertically oriented blade having a first cutting edge and an oppositely facing second cutting edge, the first and second cutting edges of the vertical blade extending in the plane of the handle, the vertically oriented blade has a first end attached to the handle and an opposing free second end, the vertically oriented blade including a bulbous tip at the first and second ends of the blade, wherein the vertically oriented blade extends from the handle in 180° opposite direction from the horizontally oriented blade, further wherein the cutting planes of the horizontally oriented blade and the vertically oriented blade extend orthogonally with respect to the handle plane and with respect to each other.

2. The uncinectomy knife of claim 1, wherein said bulbous tips each comprise a sphere.

3. The uncinectomy knife of claim 1, wherein the knife is made from stainless steel.

4. A method of removing an uncinate process from an ethmoid bone using an uncinectomy knife, comprising the steps of:
    providing an uncinectomy knife, the uncinectomy knife having:
        an elongated handle having a first end and an opposing second end, the handle defining a handle plane;
        a horizontally oriented blade extending orthogonally from the first end of the handle, the horizontally oriented blade having a first cutting edge and an oppositely facing second cutting edge, the first and second cutting edges of the horizontally oriented blade facing perpendicular to the handle plane, wherein the horizontally oriented blade has a first end attached to the handle and an opposing free second end, the horizontally oriented blade including a bulbous tip at the first and second ends of the blade; and
        a vertically oriented blade extending orthogonally from the second end of the handle, the vertically oriented blade having a first cutting edge and an oppositely facing second cutting edge, the first and second cutting edges of the vertical blade extending in the plane of the handle, the vertically oriented blade has a first end attached to the handle and an opposing free second end, the vertically oriented blade including a bulbous tip at the first and second ends of the blade, wherein the vertically oriented blade extends from the handle in 180° opposite direction from the horizontally oriented blade, further wherein the cutting planes of the horizontally oriented blade and the vertically oriented blade extend orthogonally with respect to the handle plane and with respect to each other;
    inserting the vertically oriented blade into a nostril passage of a patient;
    separating the upper and lower parts of the uncinate process to the lacrimal bone using an up and down cutting motion of the vertically oriented blade;
    reversing the knife;
    using the horizontally oriented blade to separate attachment of the uncinate superiorly from the lacrimal bone and the lower part from the inferior turbinate bone using a forward and reverse cutting motion of the horizontally oriented blade.

* * * * *